(12) United States Patent
Schmidt et al.

(10) Patent No.: US 6,829,933 B1
(45) Date of Patent: Dec. 14, 2004

(54) DEVICE FOR DETERMINING THE DENSITY OF AN ELECTROLYTE

(75) Inventors: Heribert Schmidt, Emmendingen (DE); Dirk Uwe Sauer, Freiburg (DE)

(73) Assignee: Fraunhofer Gesellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 09/937,965

(22) PCT Filed: Mar. 22, 2000

(86) PCT No.: PCT/DE00/00918

§ 371 (c)(1),
(2), (4) Date: Jan. 25, 2000

(87) PCT Pub. No.: WO00/60331

PCT Pub. Date: Oct. 12, 2000

(30) Foreign Application Priority Data

Apr. 3, 1999 (DE) .......................... 199 15 328

(51) Int. Cl.⁷ ................................. G01N 9/26
(52) U.S. Cl. .......................... 73/438; 429/90
(58) Field of Search .................. 73/438, 439, 302; 429/90, 91; 324/432

(56) References Cited

U.S. PATENT DOCUMENTS

| | | |
|---|---|---|
| 2,072,916 A | 3/1937 | Willach et al. ............... 73/438 |
| 3,074,277 A | 1/1963 | Hill ............................. 73/439 |
| 4,949,572 A * | 8/1990 | Wilen et al. ................. 73/439 |
| 5,580,675 A * | 12/1996 | Rouhani ........................ 429/90 |

FOREIGN PATENT DOCUMENTS

| | | |
|---|---|---|
| DE | 2415033 | 10/1974 |
| DE | 3030779 | 3/1982 |
| FR | 1429352 | 5/1966 |

OTHER PUBLICATIONS

The International Bureau of WIPO, International Preliminary Examination Report, Dec. 28, 2001, pp. 1–6.

* cited by examiner

Primary Examiner—John E. Chapman
(74) Attorney, Agent, or Firm—Stevens, Davis, Miller & Mosher, LLP

(57) ABSTRACT

The invention relates to a device (2) for determining the density of an electrolyte (4). Said device (2) comprises at least two immersion tubes (9, 10) provided with an open orifice (52) and immerging at different depths in the electrolyte (4), whereby said immersion tubes can be respectively filled with gas to a depth (21, 22) which is allocated thereto and each tube has a different gas depth (d) with respect to the other. A least one differential pressure sensor (16) is used to define the difference in pressure inside the immersion tubes (9, 10). An electrode (11, 19) is respectively provided inside the immersion tubes (9, 10), whereby said electrode is connected to a voltage source (5, 35) in order to produce the required depth (21, 22) of gas so that said immersion tubes (9, 10) can be filled therewith upon contact with the electrolyte(4).

26 Claims, 15 Drawing Sheets

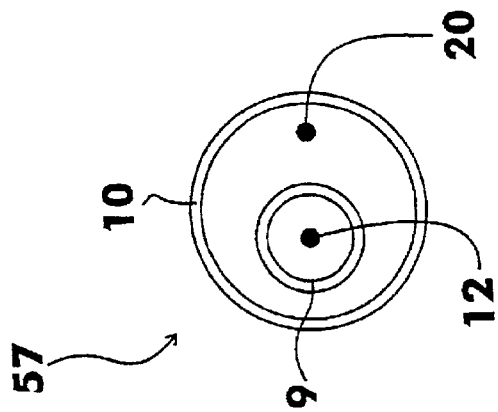
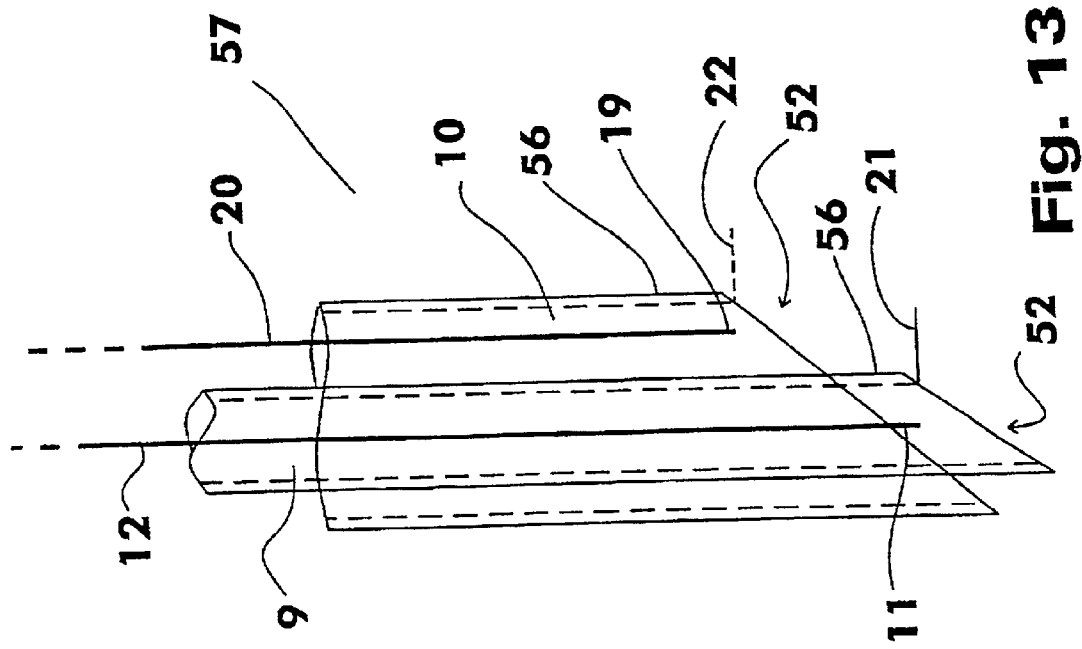

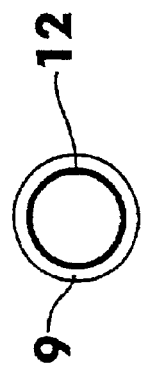
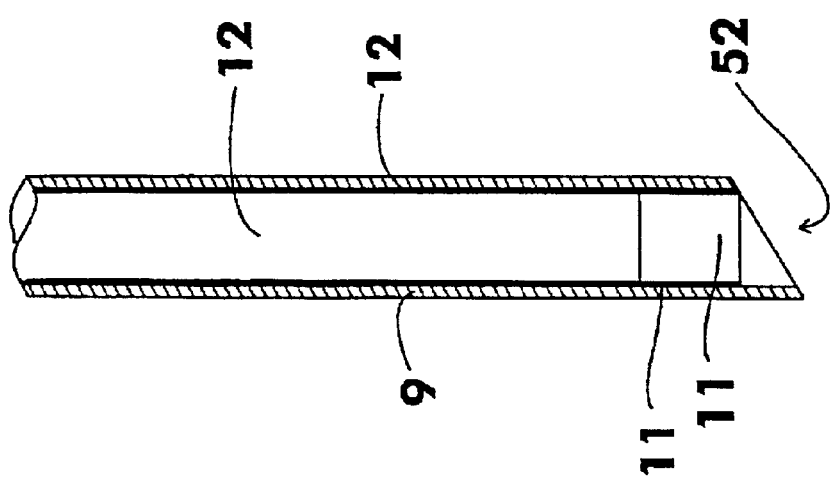

DEVICE FOR DETERMINING THE DENSITY OF AN ELECTROLYTE

The invention concerns a device for determining the density of an electrolyte with at least two immersion tubes submerging with an open tube opening up to different depths into the electrolyte, which can be filled with gas up to an assigned gas depth and which have a gas depth difference with respect to each other, and with at least one pressure sensor for determining the pressure difference in the immersion tubes.

A device of this kind is already known, for example, from the "Handbook of Industrial Measurement Technology" by Prof. Dr. P. Profos and published by Vulkan Publishers of Essen, which appeared in the year 1987. In the article entitled "Hydrostatic Measuring Methods," which appeared in the fourth edition on pages 639 to 640, is disclosed a device, wherein an inert gas is injected via two immersion tubes, which are submerged in a liquid at different depths. The gas flow coming out of the deeper-lying tube opening has to overcome a greater hydrostatic pressure of the liquid than the one coming out of the higher-lying tube opening. The differential pressure which exists in the tubes is only dependent upon the density of the liquid. Via a connection of the immersion tubes to the differential pressure manometer can be calculated the density of the liquid. The constant injection of inert gas, however, requires a technically complicated gas pressure supply, which is prone to errors and causes a high energy consumption. Furthermore, the gas pressure supply is bulky because of its individual volume. Another disadvantage consists in that the constant gas generation in the liquid is frequently undesirable with respect to corrosion and the introduction of foreign substances.

German patent publication 3,030,779 discloses a process for measuring the charge state of electric accumulators as well as a device for carrying out the process. The device disclosed therein comprises a vertically arranged pressure-resistant tube, which is filled with gas or liquid, and to which gas bellows are connected at different heights. Between the connection points of the gas bellows is arranged a pressure transducer, which is connected via a measuring line to an external electronic meter. The pressure transducer seals off the tube, so that the meter shows the differential pressure existing at the gas bellows and therefore an average density existing between the gas bellows. The individual volume required by the device, however, is considerable because of the transverse expansion of the gas bellows so that a device of this kind cannot be used, for example, in narrow cramped lead accumulators. Also, because of the individual volume of the gas bellows, inaccuracies occur even with respect to the exact immersion depth of the gas bellows.

The object of the invention is to provide a device of the kind described above, which allows a simple, less error-prone gas filling of the immersion tubes and which has a individual volume which is as small as possible.

This object is attained according to the invention in that electrodes connected to a voltage source are arranged in the interior of the immersion tubes, with which gas can be produced upon contact with the electrolyte to fill the immersion tubes up to the corresponding gas depth.

The electrochemical gas generation simplifies the filling of the immersion tubes and makes superfluous an error-prone mechanic gas pressure generation, so that annoying maintenance work can be eliminated. The arrangement of the electrodes in the interior of the immersion tubes further reduces the device in size and facilitates therefore its use in fields, which are characterized by an effective space utilization.

In a preferred embodiment, the device according to the invention has vertically-directed immersion tubes, wherein the corresponding electrode has an immersion depth which essentially coincides with the gas depth of the corresponding immersion tube.

To connect the electrodes to the electric voltage source are provided advantageous electrode connecting lines, each surrounded by an acid-resistant insulation.

In a practical further development, each electrode connecting line consists of an elastic material and has in the transverse direction a waved wire structure, so that, in a stretched position, pressure forces can be produced on an inner wall of the immersion tube to hold the corresponding electrode.

In a variation thereof, the immersion tube has in its interior an electrode fixation, which is made of an elastic plastic material, and which is connected via radially running transverse struts and a circular section connected to the transverse struts to a passage opening for guiding through the electrode connecting line, wherein the circular section is fixedly connected to the transverse struts and the length of the transverse struts is adapted to the inner diameter of the corresponding immersion tube in such a manner that) in an inserted position of the immersion tube, the holding forces necessary for the fixation can be generated.

In another variation thereof, a mounting headpiece is provided, which can be gas-tight installed on the tube opening, which has a gas outlet opening on its beveled end facing away from the immersion tube as well as a mounting area fixedly connected to the corresponding electrode.

In a preferred embodiment, the immersion tubes have beveled tube ends to simplify the discharge of the escaping gas bubbles.

In a related further development, the immersion tubes have fixed lateral passage openings, wherein in another different exemplary embodiment, a lateral grooving of the immersion tubes is provided.

At the end facing away from the electrolyte, the immersion tubes are advantageously gas-tight connected to a connecting nozzle, which is made of plastic, and which has on its side wall a line entry arranged for a gas-tight passing through of the corresponding electrode connecting line.

In an alternate exemplary embodiment, the device according to the invention has immersion tubes, which are gas-tight connected at their end facing away from the electrolyte to a connecting nozzle, which has at least by sections an electrically conducting side wall, at whose outer and inner sides the corresponding electrode connecting lines are conductively attached.

In a preferred embodiment, the electrodes, which are submerged in an aqueous electrolyte solution, are made of a material with low hydrogen surge and connected to an accumulator electrode of an accumulator, which is negative in its charged condition.

In a different exemplary embodiment, the device according to the invention comprises a DC—DC converter, which is arranged for converting a decreasing DC voltage occurring between two accumulator electrodes into a higher DC voltage and for applying the increased voltage on an electrode, on the one hand, and, on the other hand, on an opposite electrode surrounded by a microperforated sleeve tube.

For an electrochemical hydrogen gas formation, the electrodes are suitably negatively charged with respect to the opposite electrode.

As an alternative thereto, the electrodes can be positively charged with respect to the opposite electrode for the electrochemical formation of oxygen gas.

It is also appropriate to produce the electrodes and their assigned electrode connecting lines as one piece and of the same material, especially lead.

In a variation thereof, the electrode connecting line is made of copper or graphite and is connected to the corresponding electrodes by means of a soldering or welding seam.

If the electrode is made according to the invention of palladium, platinum, or a similar alloy with a merely low hydrogen surge, it is practical that the corresponding electrodes can be configured at their end areas of the corresponding electrode connecting line, wherein the non-coated section of the corresponding electrode connecting line is enclosed by an acid-resistant insulation.

In a modification of this exemplary embodiment, the corresponding electrode is configured as a coating of an end area of the inner wall of the corresponding immersion tube, to which a coating, which acts as an electrode connecting line, is electrically conductively connected.

In another practical further development, the device comprises a temperature sensor, which is submerged in the electrolyte, wherein the temperature sensor and the or each pressure sensor is connected to a data processor for digitalizing the measurement signals, which is connected via a data bus to a microcontroller for calculating the charged condition from the measured acid density of the accumulator.

For an advantageously compact configuration of the device, two immersion tubes have differently dimensioned diameters, wherein the first immersion tube extends at least in part into the interior of the second immersion tube.

In another exemplary embodiment, the device according to the invention has an elastic outer hose, which stretches around the sleeve tube, the temperature sensors, and the temperature measuring line to support the two immersion tubes.

In an exemplary embodiment of the device according to the invention for measuring an acid layer, a desired number of immersion tubes and a number of pressure sensors reduced by one with respect to the number of immersion tubes are provided for measuring the pressure difference between the respective immersion tubes of a immersion tube pair, wherein the immersion tube pairs with their corresponding gas depths assigned to the pressure sensors delimit layers of the electrolyte at different depths, so that the measured data provided by the pressure sensors can be assigned to the layers.

Other practical embodiments and advantages of the invention are the object of the following description of the exemplary embodiments with reference to the figures of the drawing, wherein similar components are provided with the same reference numerals. In the drawing:

FIG. 13 shows a lateral view of a compact immersion tube arrangement according to FIG. 2;

FIG. 14 shows a cross section view of the immersion tube arrangement according to FIG. 13;

FIG. 22 shows a lateral section view of another exemplary embodiment of the immersion tube according to FIG. 18;

FIG. 23 shows a cross section view of the immersion tube according to FIG. 22;

Figure 1:
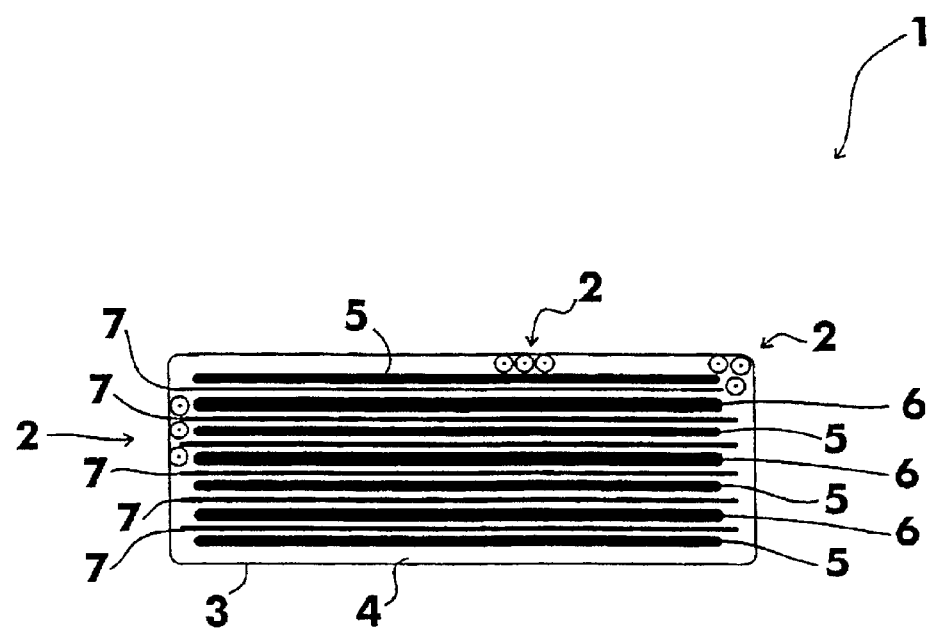
FIG. 1 shows a cross section view of a lead accumulator with several possible arrangements of the device according to the invention.

FIG. 1 shows a cross section view of a lead accumulator 1 with several possible arrangements of the device 2 according to the invention. The lead accumulator 1 comprises an accumulator housing 3, which contains a diluted sulphuric acid 4 as an electrolyte, with a specific weight of 1.0 kilogram per liter or 1.35 kilograms per liter. To configure the accumulator electrodes, lead electrodes 5 as well as lead dioxide electrodes 6, which are arranged parallel to each other in alternating order, project into the sulphuric acid 4. The lead electrode 5 consists of a lead support structure, whose surface is coated by a sponge-like porous lead layer. To improve the electric insulation, separators 7 are arranged between the accumulators 5, 6.

The sulphuric acid 4 participates directly in the electrochemical reactions of the lead accumulator 1, so that the density of the sulphuric acid 4 is directly linked to the charge state of the lead accumulator 1. If the temperature of the sulphuric acid 4 is known, the charge state of the lead accumulator can be calculated from the density. Herein, it should be taken into consideration that the sulphuric acid is not homogeneously distributed in the lead accumulator 1 and that density oscillations may occur. It his therefore advantageous to determine the acid density as indicated in FIG. 1 with several devices 2 at the same time, or with one device 2 at different time points at different points of the lead accumulator 1 to be able to gather detailed information on the charge state of the lead accumulator 1. Measurements of the acid layers wherein the density of the sulphuric acid 4 is measured at different depths of the electrolyte are especially interesting in this connection. For this reason, the device 2 according to the invention has a small individual volume in comparison with the entire lead accumulator 1. The density of the sulphuric acid 4 can therefore be determined simultaneously at several points and especially at different depths.

Figure 2:
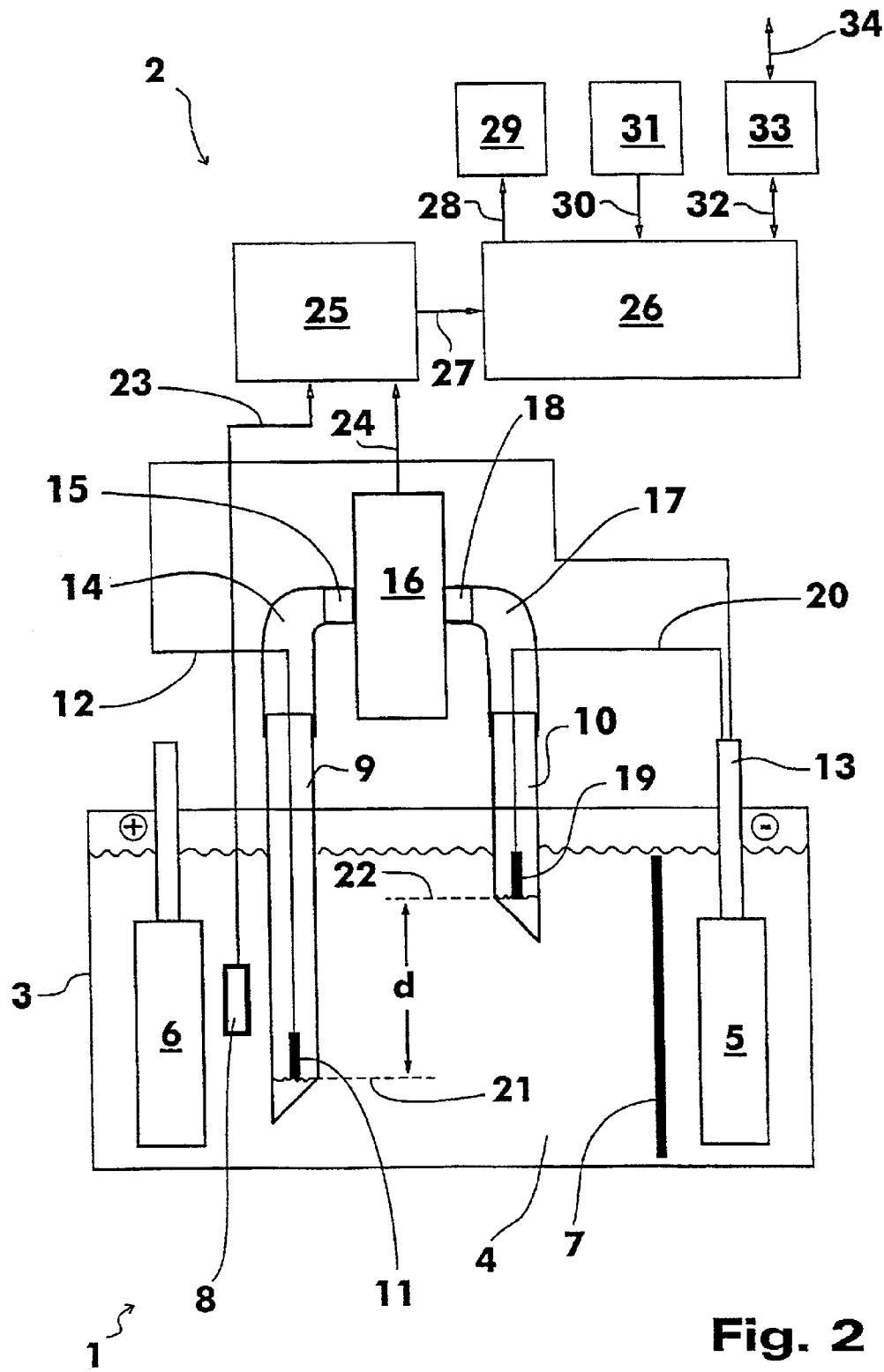
FIG. 2 shows a schematic illustration of a first exemplary embodiment of the device according to FIG. 1.

FIG. 2 shows a schematic illustration of a first exemplary embodiment of the device 2 according to FIG. 1. In the accumulator housing 3 are provided, aside from the lead electrode 5, the lead dioxide electrode 6, the separator 7, and a temperature sensor 8 for measuring the temperature of the sulphuric acid 4. Furthermore, a vertical first immersion tube 9 and a vertical second immersion tube 10 can be seen, which are submerged at different depths into the sulphuric acid 4.

Within the first immersion tube 9 is concentrically arranged a first electrode 11, which is connected via a first electrode connecting line 12 to a lead electrode connection 13 of the lead electrode 5. At its end, which projects out of the sulphuric acid 4, the first immersion tube 9 has a first hose connection 14, which connects the first immersion tube 9 with a first inlet nozzle 15 of a pressure sensor configured as a differential pressure sensor 16. The second immersion tube 10 is correspondingly connected via a second hose connection 17 with a second inlet nozzle 18 of the differential pressure sensor 16. A second electrode 19 arranged concentrically in the interior of the second immersion tube 10 is also connected via a second electrode connecting line 20 with the lead electrode connection 13 of the lead accumulator 5.

In the charged state of the lead accumulator 1, the lead electrode 5 is negatively charged with respect to the lead dioxide electrode 6. The magnitude of this negative potential is basically sufficient to reduce the hydronium ions to hydrogen while forming gas at the lead electrode 5. At the sponge-like porous lead coating of the lead electrode 5, a large hydrogen surge occurs, which is sufficient to inhibit the undesirable reaction.

In the shown exemplary embodiment, the first electrode 11 and the second electrode 19 are made of platinum. Platinum has a comparatively insignificant hydrogen surge so that, when the electrodes 11, 19 make contact with the aqueous sulphuric acid 4, a gaseous hydrogen is electrochemically generated, which rises within the immersion tubes 9, 10 and pushes the sulphuric acid 4 out of the interior of the immersion tubes 9, 10 until a first assigned gas depth 21 or a second gas depth 22 of the immersion tubes 9, 10 has been reached. The gas depth 21 or 22 is the depth measured from the surface of the sulphuric acid 4 up to which the immersion tube 9, 10 can be filled with gas before it exits out of the corresponding immersion tube 9 or 10, and rises to the surface in the form of bubbles by overcoming the corresponding hydrostatic pressure of the sulphuric acid 4.

If the immersion tubes 9, 10 are filled with gas up to their corresponding gas depth 21, 22, the pressure p existing in the immersion tubes 9, 10 is equal to the pressure which is produced by a liquid column of aqueous sulphuric acid 4, whose height h corresponds to the gas depth 21, 22 of the corresponding immersion tube 9, 10. The pressure of a liquid column is calculated with the aid of the gravity g according to the formula $p = \rho\, g\, h$ and is dependent upon the density p of the liquid. As shown schematically in FIG. 2, the immersion tubes 9, 10 have a fixed and preset gas depth difference d between the first gas depth 21 and the second gas depth 22. With the gas depth d via a differential pressure $\Delta p$ recorded at the differential pressure sensor 16, which corresponds to the pressure difference in the immersion tubes 9, 10, can be determined the density of the sulphuric acid 4 according to the formula $$e = \frac{\Delta p}{g\, d}.$$

In another exemplary embodiment of the device according to the invention, which is not shown, can be determined the pressure difference via two pressure sensors provided for measuring the absolute pressure in the immersion tube 9 or 10 with an additional electric or computed difference formation of the measured pressure values.

The adjustment of the corresponding electrodes 11, 19 to the corresponding gas depth 21, 22 gains particular importance. If the immersion depth of the electrodes 9, 10 is greater than the correspondingly assigned gas depth 21 or 22, a constant gas formation sets in, which burdens the charge state of the lead accumulator 1 on the one side. If the immersion depth of the electrodes 11,19 is less than the gas depth 21 or 22 of the correspondingly assigned immersion tube 9, 10, the corresponding inner pressure of the immersion tubes 9, 10 is dependent upon the corresponding gas depth 21, 22 of the immersion tubes 9, 10, so that the acid density can no longer be determined in view of the measured differential pressure via the known gas depth difference d.

To prevent unnecessary charge losses of the lead electrodes 5 and, at the same time, inaccuracies in the determination of the charge state of the lead accumulator 1, the corresponding immersion depth of the electrodes 11, 19 coincides essentially with the corresponding gas depth 21, 22 of the immersion tubes 9, 10. In this way, after the immersion tubes 9, 10 are filled with gas up to the gas depth 21, 22, the electrolytic reaction is interrupted since the sulphuric acid is no longer in contact with the electrodes 11, 19.

The charge state of the lead accumulator 1 can be calculated with the known density and temperature of the sulphuric acid 4. Therefore, the temperature sensor 8 and the differential pressure sensor 16 are connected via a temperature measuring line 23 or via a differential pressure measuring line 24 with a data processing 25. The data processing 25 digitalizes the recorded measured values with the aid of an analog-digital converter to later make available the digitalized measured values to a microcontroller 26 via a data bus 27. The microcontroller 26 is digitalized measured values to a microcontroller 26 via a data bus 27. The microcontroller 26 is connected via a cable 28 to a display unit 29, with whose aid the charge state of the lead accumulator 1 can be displayed. The microcontroller 26 is also connected via a keyboard cable 30 with a keyboard 31 and via a bidirectional data line 32 with a data interface 33, wherein the data interface 33 can be connected via an interface cable 34 to control units which are not shown for controlling any processes which depend from the charge state of the lead accumulator 1.

Figure 3:
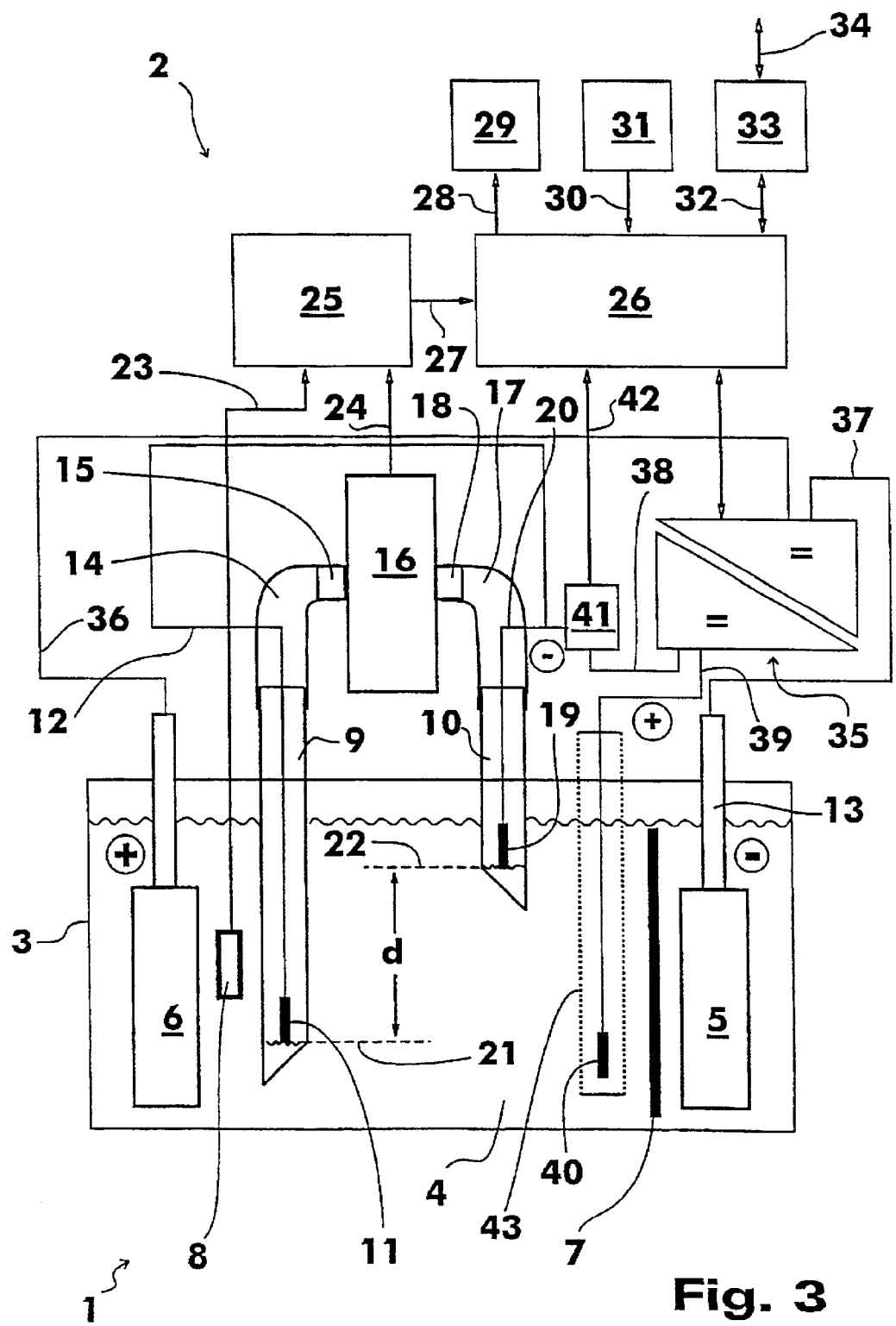
FIG. 3 shows a schematic illustration of a second exemplary embodiment of the device according to FIG. 1.

FIG. 3 shows a schematic representation of a second exemplary embodiment of the device 2 according to FIG. 1.

One can see two immersion tubes 9, 10, which are submerged at different depths in the sulphuric acid 4 of the lead accumulator 1, which have electrodes 11 or 19 arranged in their interior. In the interior of the immersion tubes 9, 10 takes place again an electrolytic dissociation of the aqueous sulphuric acid 4 while building hydrogen, so that a state of equilibrium between the inner pressure existing in the immersion tubes 9, 10 and the hydrostatic pressure is established, which develops at the assigned first gas depth 21 or the second gas depth 22.

In the modification of the exemplary embodiment shown in FIG. 2, the DC—DC converter 35 can be seen, which is connected via a lead dioxide electrode connecting line 36 and via a lead electrode connecting line 37 with the positive lead dioxide electrode 6 or with the negatively charged lead electrode 5. The DC—DC converter 35 converts the DC voltage, which decreases between the lead electrode 5 and the lead oxide electrode 6 into a higher DC voltage, which is applied with the aid of an electrode connecting line 38 or an opposite electrode connecting line 39 on the electrodes 11, 19, on the one hand, and on the positive opposite electrode 40, on the other hand.

Between the electrode connecting line 38 and the electrodes 11, 19 is provided a current measuring unit 41, which is connected via a current measuring line 42 with the microcontroller 26. With the aid of the current measuring line 41 it can be determined if a state of equilibrium has been reached. For example, the penetration of sulphuric acid 4 into the immersion tubes 9, 10 can be shown via the current flow displayed by the current measuring unit 42 as a consequence of the hydrogen development on the electrodes 11, 19. If the measuring unit 42 does not show any current flow, it can be assumed that the system is in a state of equilibrium to prevent in this way uncertainties with respect to the charge state of the lead accumulator 1.

The positive opposite electrode 40 is arranged in the interior of a microperforated sleeve tube 43, which allows the passage of the sulphuric acid 4, but prevents for the most part a contamination of the electrolyte outside the sleeve tube 42 by the positive opposite electrode 40.

The electrolysis with the aid of the DC—DC converter 35 affects both accumulator electrodes 5, 6 advantageously in the same measure. The increased DC voltage existing between the opposite electrode 40 and the electrodes 11, 19 expands further the possibility of selecting a suitable material for the electrodes 11, 19, which is limited if DC voltage is not increased to materials characterized by no hydrogen surge or a negligible hydrogen surge. Even though the materials such as, for example, platinum or palladium meet all the mentioned requirements, their use is however cost-intensive and requires additional expenditures with respect to the connection to an electrode connecting line consisting of a more cost-effective material and which will be described in more detail in the following with reference to FIGS. 5 and 6.

It is also important that the electrolyte not be contaminated by traces of dissolved electrode material. Therefore, already small quantities of dissolved gold are sufficient to considerably impair the charging or discharging process of the accumulator 1. The increased DC voltage provided now by the DC—DC converter 35 makes possible the use of lead as electrode material, so that the production costs of the electrodes are low and furthermore a contamination of the sulphuric acid 4 is prevented.

In another exemplary embodiment, which is not shown, the polarity of the electrodes 11, 19 participating in the electrolytic gas generation is inverted. In the now positively charged electrodes 11, 19 is produced therefore a gaseous oxygen, which rises in the immersion tubes 9, 10 and displaces the liquid sulphuric acid 4.

Figure 4:
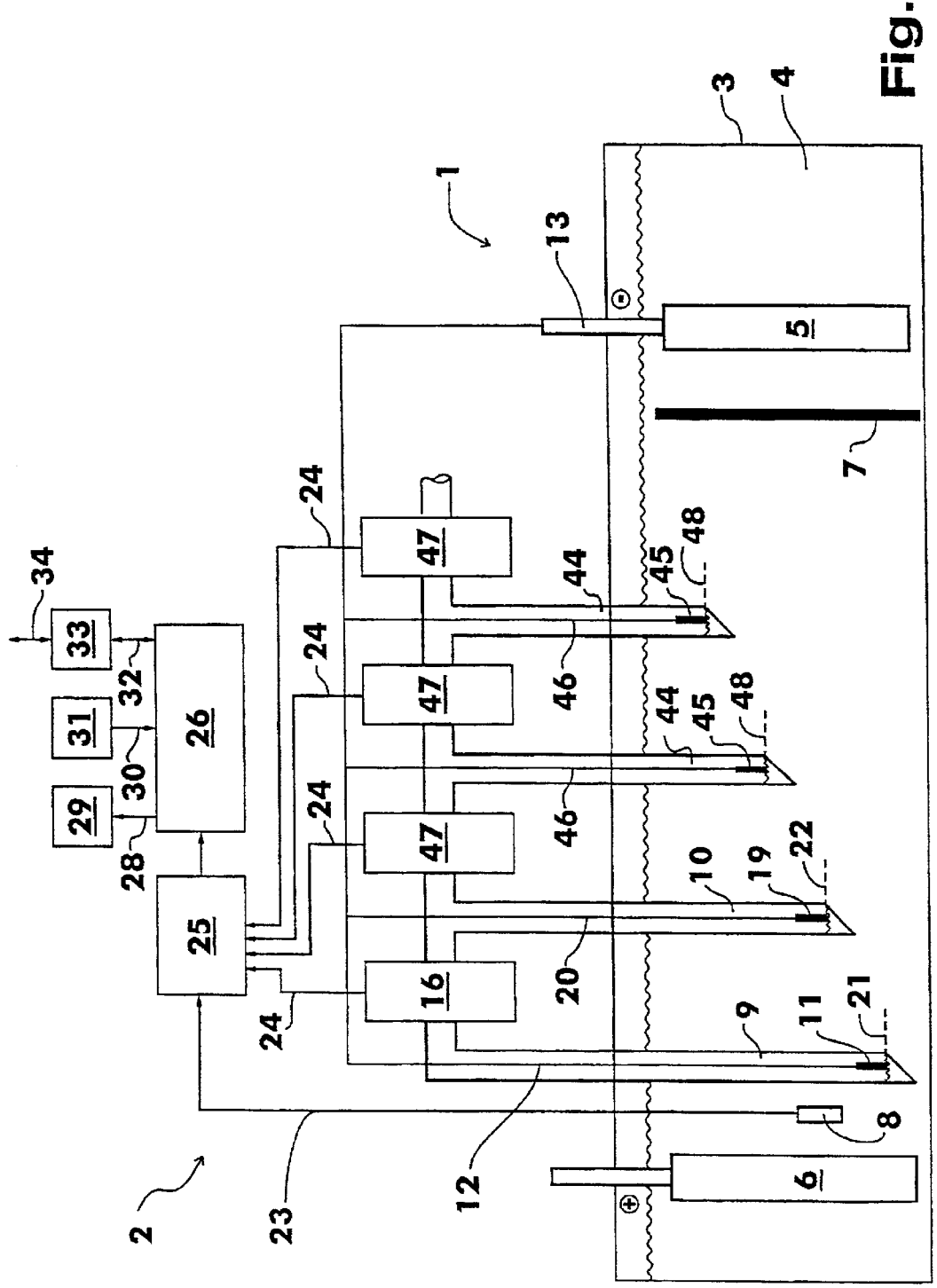
FIG. 4 shows a schematic illustration of a third exemplary embodiment of the device according to FIG. 1.

FIG. 4 shows a third exemplary embodiment of the device according to FIG. 2 and shows especially a device for measuring an acid layer within the lead accumulator 1. In contrast with the exemplary embodiments shown until now, aside from the first immersion tube 9 and the second immersion tube 10, other immersion tubes 44 with further electrodes 45 and further electrode connecting lines 46 can be seen, whose number can be increased above the measure shown in FIG. 2. Furthermore, aside from a first pressure sensor 16, further pressure sensors 47 are shown, which are arranged to measure the differential pressure which occurs between two adjacent immersion tubes 10, 44 and which are connected via differential pressure measuring lines 24 with the measured data processing 25. The immersion depth of the immersion tubes 9, 10, 44 measured from the surface of the sulphuric acid 4 is established by means of a suitable mount, wherein the immersion tubes 9, 10, 44 also have a correspondingly assigned gas depth 21, 22 or 48 with a known gas depth difference.

From the adjacent immersion tubes 9, 10, 44 can be measured the average acid densities of different acid layers, wherein the corresponding layer is delimited by the gas depths 21, 22, 48 of the adjacent immersion tubes 9, 10, 44. In the shown configuration of the device 2 according to the invention, for example, the first immersion tube 9 and the second immersion tube 10 measure the average acid density of a first layer, which is delimited by the first gas depth 21 and the second gas depth 22. A higher-positioned second layer, for example, is delimited by the gas depths 48 of the adjacent immersion tubes 44. The differential pressure sensors 16, 47 are in this way assigned to an acid layer with a known depth, so that the acid layer can be displayed via the microcontroller 26, for example, on the monitor 29.

Figure 5:
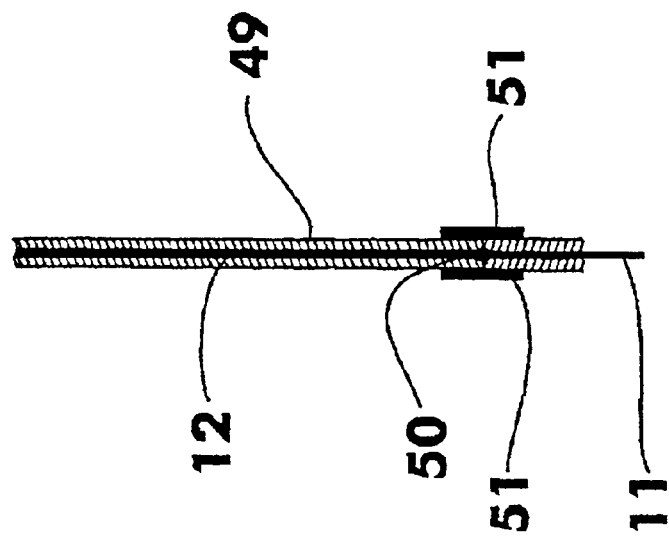
FIG. 5 shows a lateral section view of an electrode with an electrode connecting line for use in a device according to FIG. 1.

FIG. 5 shows in detail an arrangement of the electrodes 11, 19, 45 and the electrode connecting lines 12, 20, 46 using the example of the electrode 11 as well as the electrode connecting line 12. In this enlarged view, the acid-resistant hose insulation 49 of the electrode connecting line 12 made of acid-resistant plastic can be seen, which also prevents an oxidation, which would dissolve the electrode connecting line 12 over a long period of time, as well as also a poisoning of the sulphuric acid 4 by foreign metals. The electrode connecting line 12 is made of a cost-effective conducting and corrosion-resistant material such as copper or graphite, and is conductively connected at its end which extends into the immersion tube 9 with the electrode 11, which is made of a platinum alloy, by means of a soldering or welding seam 50. To prevent a voltage pairing, the soldering or welding seam 50 is protected by an additional soldering or welding insulation 51. At the end of the electrode 11 facing away from the soldering or welding seam 50, the hose insulation 49 is removed to make possible the entry of the sulphuric acid 4 into the electrode 11 and therefore the gas formation.

In an exemplary embodiment for use in a device of the invention in accordance with FIG. 3, which is not shown, the electrodes 11, 19 and the electrode connecting line 12, 20 can be formed as one piece, wherein both are made of a lead alloy. The higher DC voltage necessary for the gas formation is supplied by the DC—DC converter 35.

Figure 6:
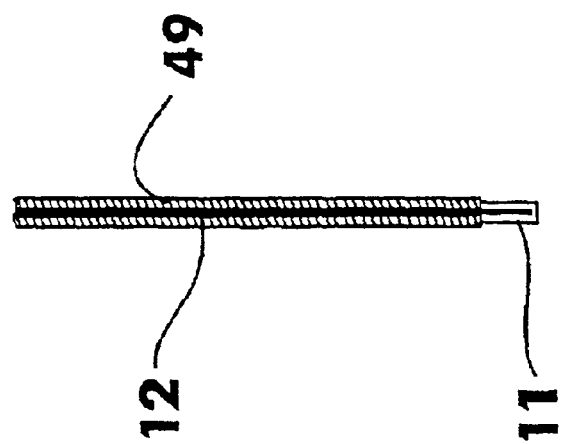
FIG. 6 shows a variant of the electrode with an electrode connecting line according to FIG. 5 in a lateral section view.

FIG. 6 shows another exemplary embodiment of the electrodes 11 according to FIG. 5, wherein the hose insulation 49 is removed in the area of the end of the electrode connecting line 12, which is configured, for example, as a copper wire, and instead is provided with a coating of platinum for forming the electrode 11. The electrode connecting line 12 is therefore conductively connected to the electrode 11, wherein the coating ensures a protection from the corrosive sulphuric acid 4.

Figure 7:
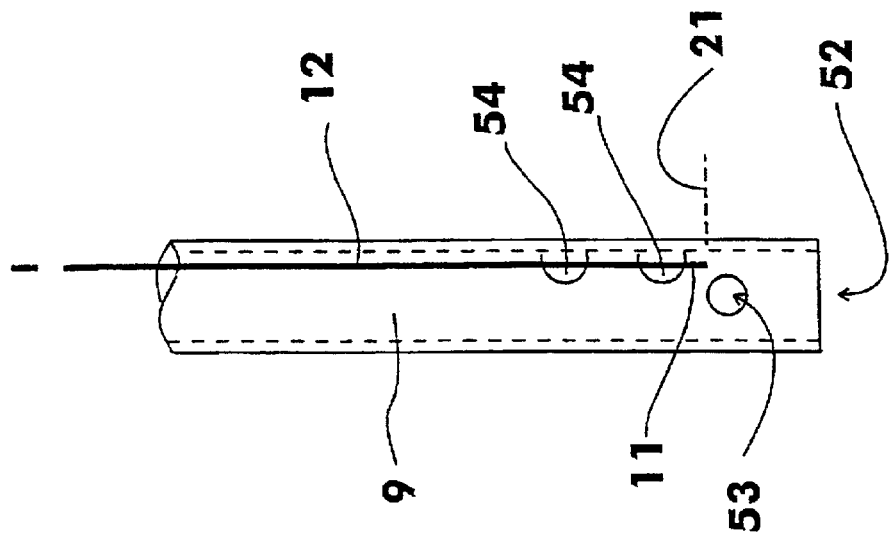
FIG. 7 shows a lateral view of a first exemplary embodiment of an immersion tube for use in a device according to FIG. 1.

FIG. 7 shows a first exemplary embodiment of the immersion tubes 9, 10, 44 in detail using the example of the immersion tube 9. To limit the gas volume necessary for the displacement of the electrolyte, the inner diameter of the immersion tube 9 should be kept as low as possible. In the shown exemplary embodiment, the outer diameter of the immersion tube 9 amounts to four millimeter with a wall thickness in the order of magnitude of a few hundred micrometer. The immersion tube 9 is made of glass or acid-resistant plastic.

The escaping gas bubbles have the tendency, because of the surface tension of the sulphuric acid 4, to remain adhered up to a certain size to a tube opening 52 of the immersion tube 9, so that the gas depth 21 is pushed downward beyond the predetermined measure. With respect to a high measurement accuracy of the device 2, such a displacement is undesirable. For this reason, a lateral passage opening 53 is provided in the immersion tube 9, which facilitates the escape of the gas bubbles, in that it imparts to the escaping bubble a lateral drive force component, which accelerates the release of the gas bubble. In this way, the gas depth 21 of the immersion tube 9 is established essentially via the upper limit of the passage opening 53. The electrode 11 and the electrode connecting line 12 are concentrically arranged in the immersion tube 9, wherein appropriate mounting measures will be described in the following with reference to FIGS. 19 to 24.

Figure 8:
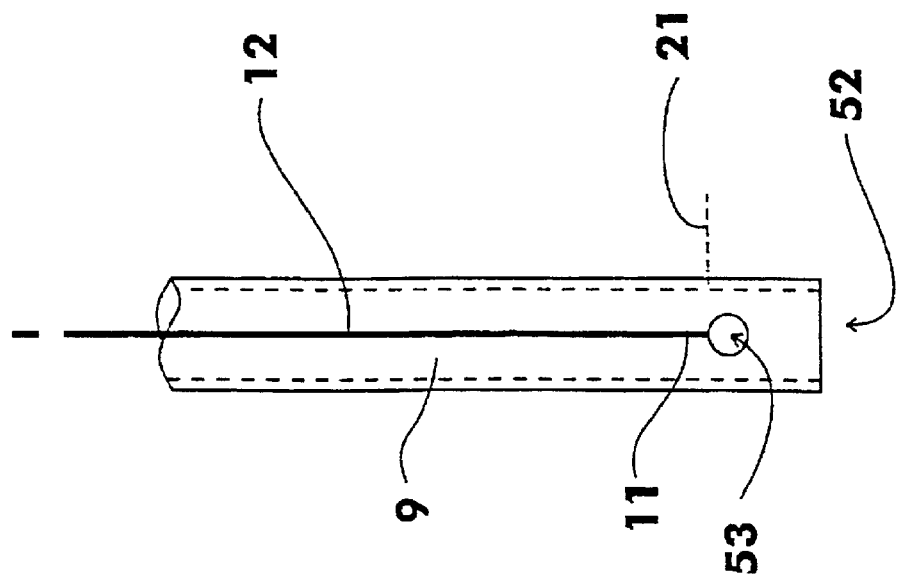
FIG. 8 shows a variant of the immersion tube according to FIG. 7 in a lateral view.

FIG. 8 shows another exemplary embodiment of the immersion tube 9 according to FIG. 7. In the configuration shown herein, the electrode 11 and the electrode connecting line 12 no longer run concentrically within the immersion tube 9, but extend along the inner tube wall to which they are fixed via a suitable bond 54, for example, with the aid of an acid-resistant plastic adhesive or glass drop. To prevent measurement inaccuracies, on the one hand, and a constant energy demand on the lead accumulator 1, on the other hand, the electrode 11 is aligned with respect to the upper limit of the passage opening 53.

Figure 9:
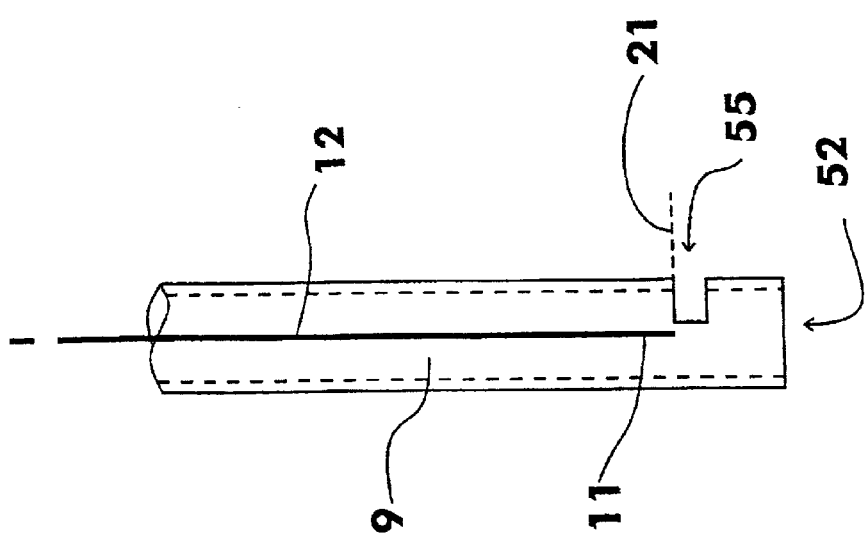
FIG. 9 shows a lateral view of a second exemplary embodiment of an immersion tube for use in a device according to FIG. 1.

FIG. 9 shows another exemplary embodiment of the immersion tube 9, 10, 44 in detail using the example of the immersion tube 9. The shown exemplary embodiment has a grooving 55 introduced on the side of the immersion tube 9, whose upper edge establishes the gas depth 21 of the immersion tube 9 and which is arranged flush with respect to the electrode 11. The purpose of the grooving 55 is again directed to make possible for the gas bubbles an easier release from the tube opening 52 with the aid of a laterally directed drive force component.

Figure 10:
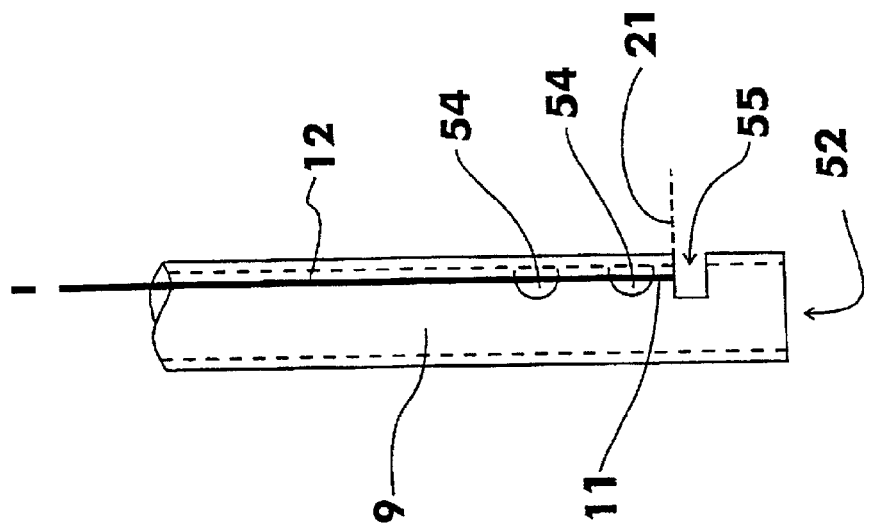
FIG. 10 shows a variant of the immersion tube according to FIG. 9 in a lateral view.

FIG. 10 shows another configuration of the immersion tube 9 according to FIG. 9, wherein however the electrode 11 and the electrode connecting line 12 run off-center along the tube wall and are attached to the same via suitable bonds 54.

Figure 11:
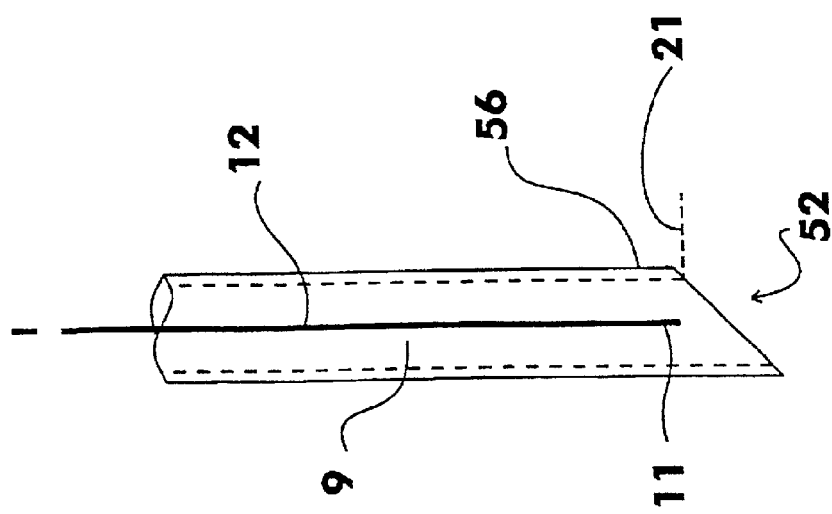
FIG. 11 shows a lateral view of a preferred exemplary embodiment of an immersion tube for use in a device according to FIG. 1.

FIG. 11 shows a preferred exemplary embodiment of the immersion tubes 9, 10, 44 using the example of the immersion tube 9, which has a beveled tube mouth 52. In this case, the beveling accelerates the release of the gas bubbles in that the drive force of the gas bubbles, which acts in all directions, finds a lesser expansion resistance after exceeding the gas depth 21 on one side because of the shorter side wall 56 of the immersion tube 9.

Figure 12:
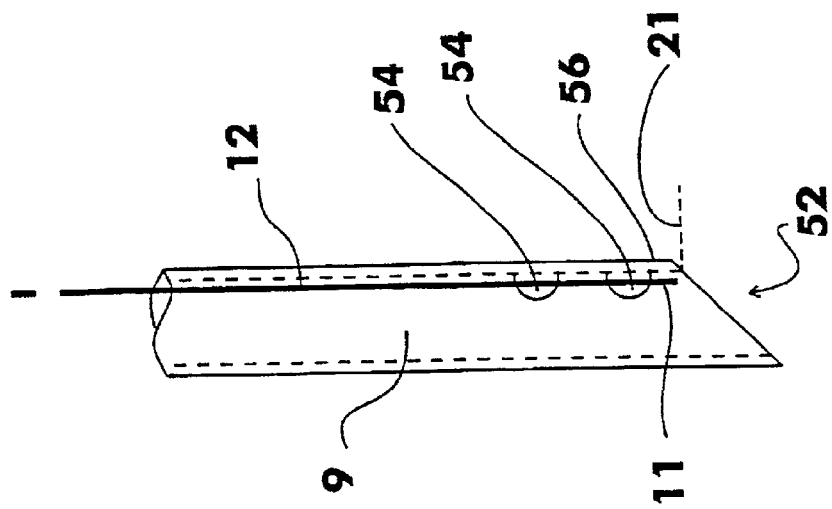
FIG. 12 shows a variant of the immersion tube according to FIG. 11 in a lateral view.

FIG. 12 shows another configuration of the immersion tube 9 according to FIG. 11, wherein the electrode 11 and the electrode connecting line 12 are attached to the interior of the immersion tube 9 at the shorter side wall 56 via the bond 54. In this configuration, the alignment of the electrode 11 to the gas depth 21 is simplified. If the electrode 11, when the tube opening 52 is beveled, is already arranged on the shorter side wall 56, the customizing of the tube opening 52 effects a cutting of the electrode 11 at the height of the shorter side wall 56, so that the immersion depth of the electrode 11 coincides with the gas depth 21.

FIGS. 13 and 14 show a lateral view or a cross section view of a compact immersion tube arrangement 57 for use in a device according to FIG. 2. The immersion tube arrangement 57 includes a first immersion tube 9 and a second immersion tube 10, wherein the diameter of the second immersion tube 10 is greater than the one of the first immersion tube 9, and the first immersion tube 9 extends within the second immersion tube 10. The first immersion tube 9 and the second immersion tube 10 have also beveled tube openings. To supply different gas depths 21, 22, the first immersion tube 9 projects out of the tube opening 52 of the second immersion tube 10.

Figure 16:
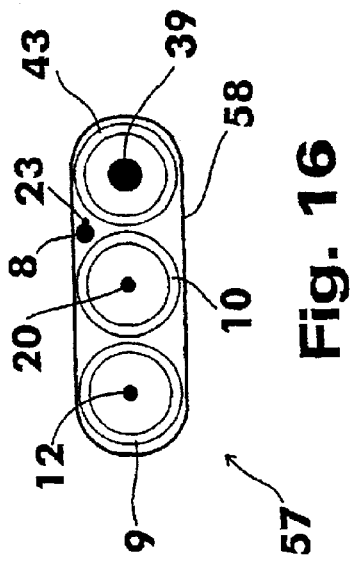
FIG. 16 shows a cross section view of the immersion tube arrangement according to FIG. 15.
Figure 15:
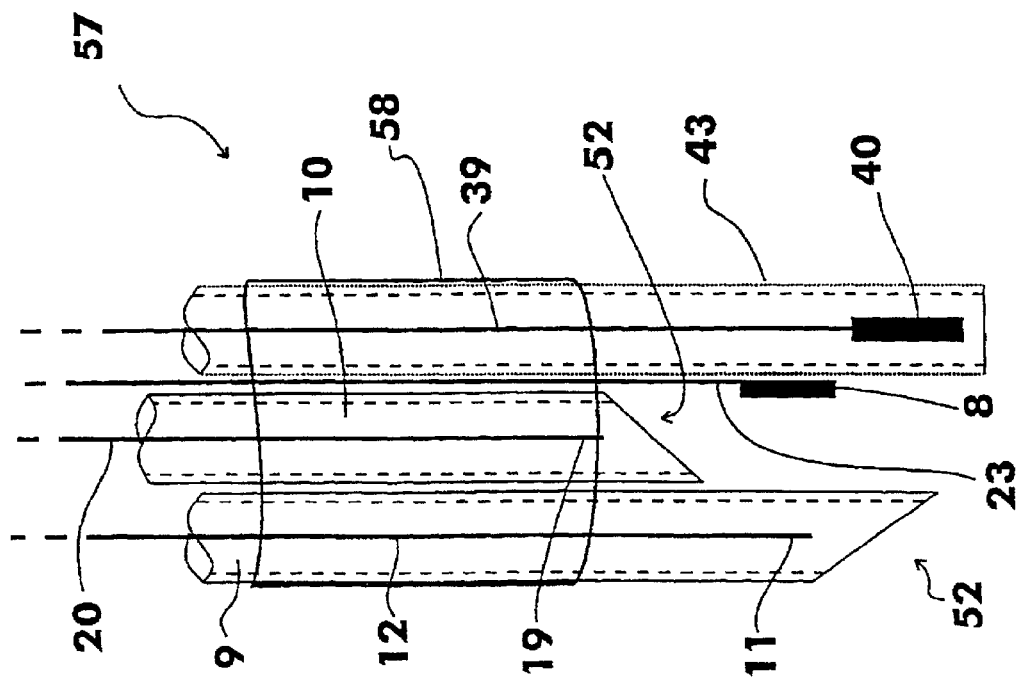
FIG. 15 shows a lateral view of a compact immersion tube arrangement according to FIG. 3.

FIGS. 15 and 16 show a lateral view or a cross section view of another compact immersion tube arrangement 57 for use in a device 2 according to FIG. 3. Herein, the first immersion tube 9, the second immersion tube 10, and the opposite electrode 40 enclosed by the sleeve tube 43 are arranged side by side and are fixed by an encompassing elastic external hose 58 made of an acid-resistant plastic. As is particularly shown in FIG. 16, the external hose 58 encompasses also the temperature sensor 8 and its temperature measuring line 23 which, to save space, are however arranged offset with respect to the electrodes 11, 19, 40, which are arranged in one line.

Figure 17:
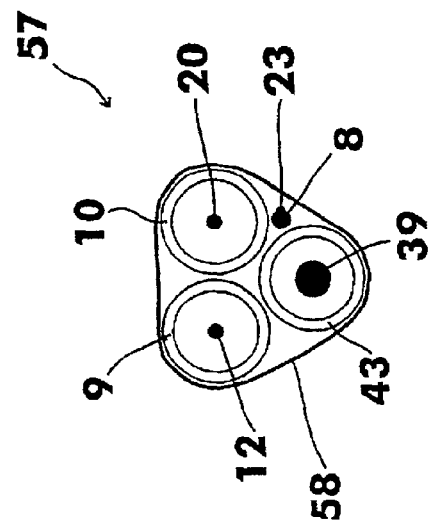
FIG. 17 shows a variant of the immersion tube arrangement according to FIG. 16.

FIG. 17 shows another exemplary embodiment of the immersion tube arrangement 57 according to FIGS. 15 and 16, wherein the sleeve tube 43 is laterally displaced and is arranged between the first immersion tube 9 and the second immersion tube 10.

Figure 19:
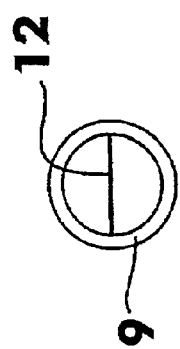
FIG. 19 shows a cross section of the immersion tube according to FIG. 18.
Figure 18:
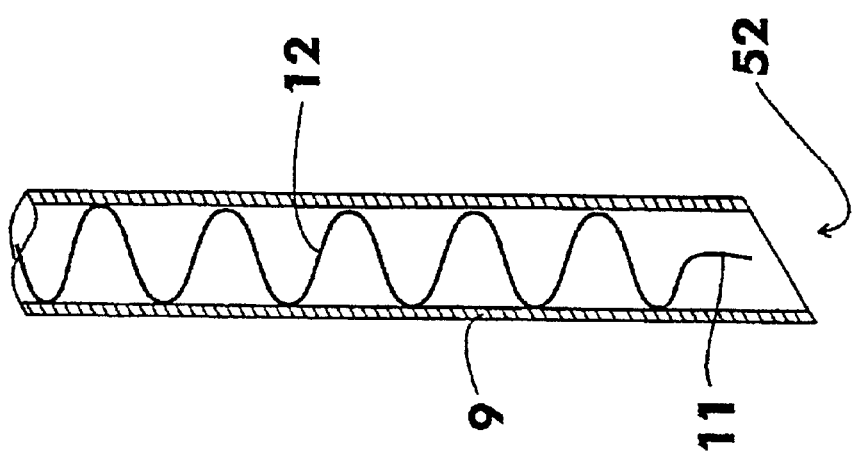
FIG. 18 shows a lateral section view which demonstrates the mounting of the electrode in the immersion tube.

FIGS. 18 and 19 show the mounting of the electrode connecting line 12, 20, 46 as well as of the electrodes 11, 19, 45 in the immersion tubes 9, 10, 44 using the example of the immersion tube 9, the electrode 11, as well as the electrode connecting line 12 in a lateral section view with respect to a cross section view. The electrode connecting line 12 has a waved structure, which because of the elastic material properties of the electrode connecting line 12 effects a spring-like pulling together with an increase of the lateral expansion of the electrode connecting line 12. This lateral expansion, however, is limited by the inner diameter of the immersion tube 9 so that pressure forces in the interior of the immersion tube 9 are generated, with whose help the electrode connecting line 12 and the electrode 11 are held in the immersion tube 9.

Figure 21:
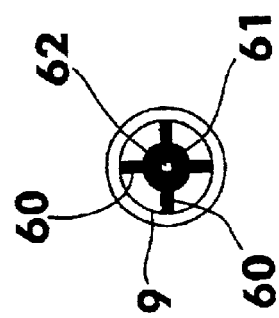
FIG. 21 shows a cross section view of the immersion tube according to FIG. 20.
Figure 20:
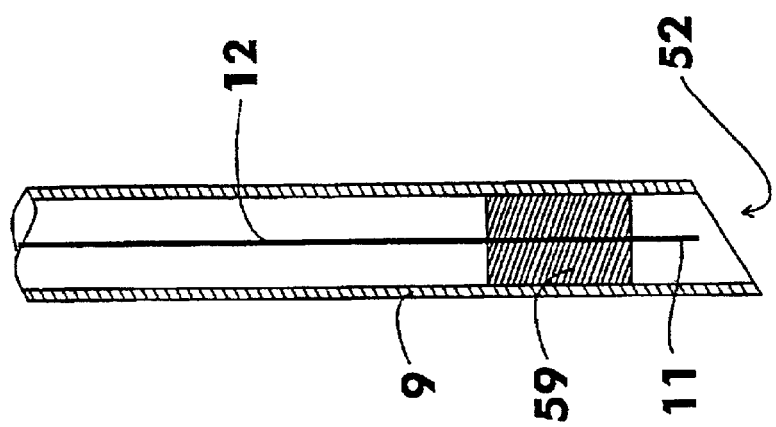
FIG. 20 shows a lateral section view of another exemplary embodiment of the immersion tube according to FIG. 18.

FIGS. 20 and 21 show another configuration of the electrode mount according to FIG. 18 in a lateral section view with respect to a cross section view. The electrode connecting line 12 runs concentrically in the interior of the immersion tube 9 and is held by an electrode mount at the area of its end. The electrode mount 59 is made of an acid-resistant elastic plastic and has radially running transverse braces 60 and a circular section 61, which has a central passage opening 62 for guiding through the electrode connecting line 12.

To fix the electrode 11, the electrode connecting line 12 is first guided through the passage opening 62 and connected, for example, by a fixed bonding, with the electrode mount 59. As an alternative, the mentioned connection can be produced already when manufacturing the electrode mount 59 by incorporating the electrode connecting line 12 into an injection molding process. The electrode mount 59 is then pressed into the tube opening 52. In this way, the electrode mount 59 can be adapted to the inner diameter of the immersion tube 9 so that the transverse braces 60 are impinged with pressure when pressing in, so as to fixedly align the electrode 11 attached to the electrode mount 59 with respect to the gas depth 21.

FIGS. 22 and 23 show another configuration of the electrode connecting line 12 as well as the electrode 11 in a lateral section view with respect to a transverse section view. It can be seen that the electrode connecting line 12 as well as also the electrode 11 are configured as a coating of the inner wall of the immersion tube 9, wherein the lower end of the electrode 11 is aligned flush to the gas depth 21 of the immersion tube 9.

Figure 24:
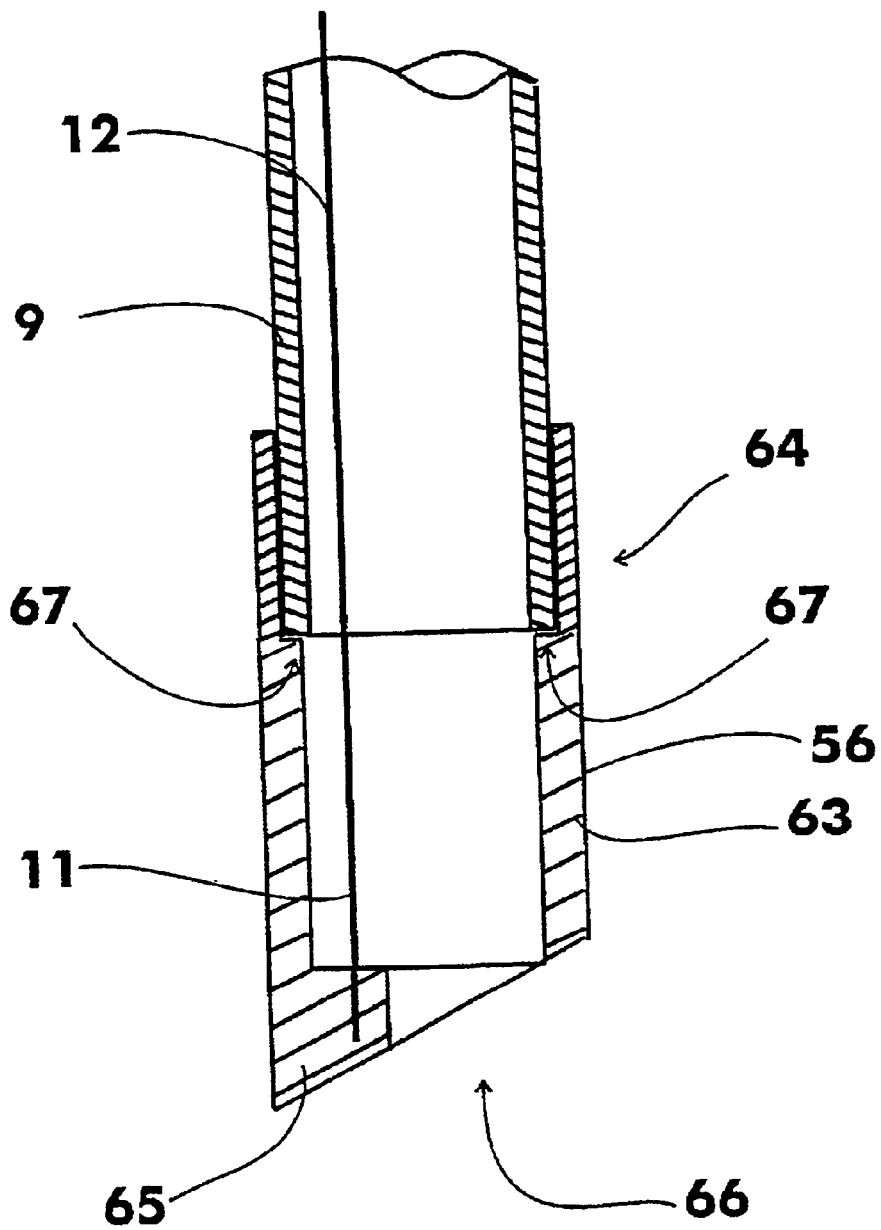
FIG. 24 shows a lateral section view of an immersion tube with a mounting headpiece for fixing the corresponding electrode.

FIG. 24 shows a lateral section view of the immersion tube 9 as well as a mounting headpiece 63 of plastic. The mounting headpiece 63 includes a receiving area 64 for connection to the immersion tube 9 and a fixing area 65, which is fixedly connected to the electrode 11 and is delimited by a beveled gas outlet opening 66. The receiving area 64 is arranged for a gas-tight enclosure of the immersion tube 9 and has a stop extension 67, which simplifies the installation of the mounting headpiece 63. The upper edge of the fixing area 65 is arranged aligned with respect to the shorter side wall 56 of the mounting head piece 63, so that the exposed area of the electrode 11, which is accessible to the sulphuric acid 4, ends flush with the shorter side wall 56.

Figure 27:
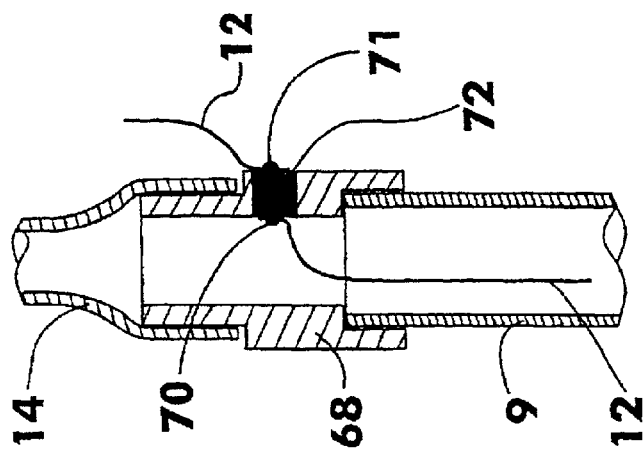
FIG. 27 shows a lateral section view of an immersion tube projecting out of the electrolyte solution with a connecting nozzle made of plastic, which has a metallic line section.
Figure 26:
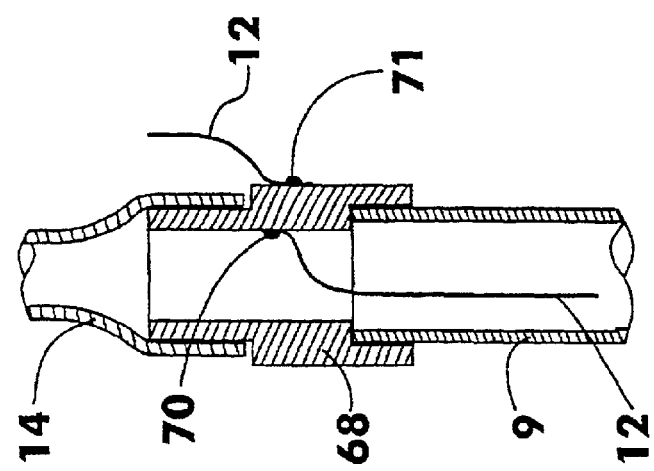
FIG. 26 shows a lateral section view of an immersion tube projecting out of the electrolyte with a metallic connecting nozzle.
Figure 25:
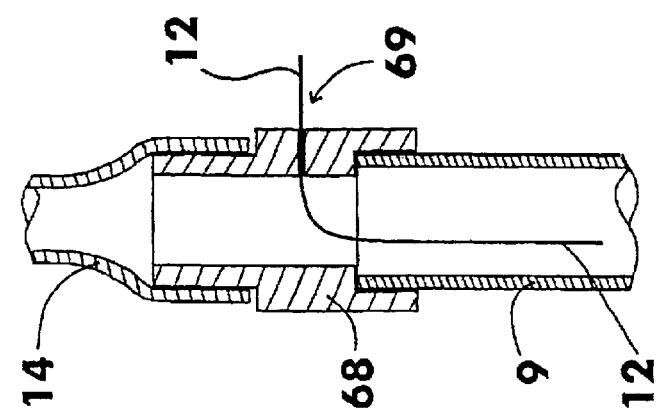
FIG. 25 shows a lateral section view of an immersion tube end projecting out of the electrolyte with a connecting nozzle made of plastic.

FIGS. 25, 26, and 27 show different exemplary embodiments of the current supply for the electrodes 11, 19, 45 arranged in the gas-tight immersion tubes 9, 10, 44.

FIG. 25 shows a connecting nozzle 68, which is provided for the gas-tight connection of the immersion tube 9 with the hose connection 14. The shown connecting nozzle 68 is made of acid-resistant non-conducting plastic and has a line entry 69 for guiding through the electrode connecting line 12. The line entry 69 can be produced, for example, via a simple punching through of the side wall of the connecting nozzle 68, wherein the line entry 69 is gas-tight enclosed after punching through and leading through the electrode connecting line 12.

FIG. 26 shows a metallic connecting nozzle 68 for the gas-tight connection of the immersion tube 9 with the hose connection 14, which has in its interior an internal soldering point 70 for connecting the part of the electrode connecting line 12, which extends into the immersion tube 9. Opposite to the internal soldering point 70 is an external soldering point 71 for electrically connecting the electrode 11 with the bioelectrode connection 13 or with the current measuring unit 41.

FIG. 27 shows a connecting nozzle 68 of plastic, which has a metallic line section 72 for connecting the electrode 11. The line section 72 is introduced gas-tight into the connecting nozzle 68 and has an internal soldering point 70 as well as an external soldering point 71, to connect the electrode 11 arranged in the interior of the immersion tube 9 with any desired external switch.

What is claimed is:

1. Device for determining the density of an electrolyte (4) with at least two immersion tubes (9, 10, 44) submerged with an open tube opening (52) at different depths into the electrolyte (4), which can be filled with gas up to an assigned depth (21, 22, 48) and have a fixed gas depth difference (d), and with at least one pressure sensor (16) for determining the pressure difference in the immersion tubes (9, 10, 44), wherein a voltage source (5, 35) is connected to electrodes (11, 19, 45) is arranged in the immersion tubes (9, 10, 44), with which gas can be generated upon contact with the electrolyte (4) for filling the immersion tubes (9, 10, 44) up to the corresponding gas depth (21, 22, 48).

2. Device according to claim 1, wherein the immersion tubes (9, 10, 44) are vertically aligned and the corresponding electrode (11, 19, 45) has an immersion depth which essentially coincides with the gas depth (21, 22, 48) of the corresponding immersion tube (11, 19, 45).

3. Device according to claim 2, wherein the corresponding electrode connecting line (12, 20, 46) comprises an elastic material and has a waved wire structure in the transverse direction, so that pressure forces can be generated in a stretched position via spring forces which set in on an inner wall of the corresponding immersion tube (9, 10, 44) for holding the corresponding electrode (11, 19, 45).

4. Device according to claim 1, wherein electrode connecting lines (12, 20, 46) are provided for connecting the electrodes (11, 19, 45), which electrode connecting lines are surrounded by an acid resistant insulation (49), to the electric voltage source (5, 35).

5. Device according to claim 4, wherein the corresponding electrode connecting line (12, 20, 46) consists of an elastic material and has a waved wire structure in the transverse direction, so that pressure forces can be generated in a stretched position via spring forces which set in on an inner wall of the corresponding immersion tube (9, 10, 44) for holding the corresponding electrode (11, 19, 45).

6. Device according to claim 4, with an electrode fixture (59) made of plastic arranged in the interior of the corresponding immersion tube (9, 10, 44), which has radially running transverse struts (60) and a circular section (61) connected with the transverse struts (60) for guiding through the corresponding electrode connecting line (12, 20, 46), wherein the circular section (61) is fixedly connected with the electrode connecting line (12, 20, 46) and the length of the transverse struts (60) is adapted to the inner diameter of the corresponding immersion tube (9, 10, 44) in such a way that when the immersion tube (9, 10, 44) is in its inserted position, the holding forces necessary for fixing the corresponding electrode (11, 19, 45) can be generated.

7. Device according to claim 4, wherein a gas-tight insertable mounting headpiece (63) is provided, which can be inserted gas-tight on the tube opening (52) of the corresponding immersion tube (9, 10, 44), which has a gas outlet opening (66) on its beveled end facing away from the corresponding immersion tube (9, 10, 44) as well as a fixing area (65) fixedly connected to the corresponding electrode (11, 19, 45).

8. Device according to claim 4, wherein the immersion tubes (9, 10, 44) have beveled tube openings (52) to simplify the release of escaping gas bubbles.

9. Device according to claim 4, wherein the immersion tubes (9, 10, 44) have a lateral passage opening (53) to simplify the release of escaping gas bubbles.

10. Device according to claim 4, wherein the immersion tubes (9, 10, 44) have a lateral grooving (55) to simplify the release of escaping bubbles.

11. Device according to claim 4, wherein the corresponding immersion tube (9, 10, 44) is gas-tight connected at its end facing away from the electrolyte (4) with a connecting nozzle (68), which is made of plastic and has a line entry (69) arranged on its side wall for the gas-tight introduction of the corresponding electrode connecting line (12, 20, 46).

12. Device according to claim 4, wherein the corresponding immersion tube (9, 10, 44) is gas-tight connected with a connecting nozzle (68) on its side facing away from the electrolyte (4), which has an at least average electrically conducting side wall (68, 72), on whose exterior and interior is conductively attached the corresponding electrode connecting line (12, 20, 46).

13. Device according to claim 4, wherein the electrodes (11, 19, 45), which are submerged into an aqueous electrolyte solution (4), are made of a material with a low hydrogen surge and are connected to an accumulator electrode (5) of an accumulator (1), which is negative in its charged position.

14. Device according to claim 4, with a DC—DC converter (35), which is arranged for converting a DC voltage decreasing between two accumulator electrodes (5, 6) into a higher DC voltage and, which is arranged for applying the increased voltage on the electrodes (11, 19, 45), on the one hand, and, on the other hand, on an opposite electrode (40), wherein the opposite electrode (40) is surrounded by a microperforated sleeve tube (43).

15. Device according to claim 14, wherein the electrodes (11, 19, 45) are submerged into an aqueous electrolyte solution and are negatively charged with respect to the electrochemical hydrogen gas formation with respect to the opposite electrode (40).

16. Device according to claim 15, wherein the electrodes (11, 19, 45) and the correspondingly assigned electrode connecting lines (12, 20, 46) are configured as one piece and are made of the same material.

17. Device according to claim 15, wherein the electrodes (11, 19, 45) and the corresponding assigned electrode connecting lines (12, 20, 46) are configured as one piece and are made of lead.

18. Device according to claim 14, wherein the electrodes (11, 19, 45) are submerged into an aqueous electrolyte solution and are positively charged with respect to the opposite electrode (40) for the electrochemical oxygen gas formation.

19. Device according to claim 14, which has an elastic outer hose (58), which encompasses as a support two immersion tubes (9, 10), the sleeve tube (43), a temperature sensor (8), and a temperature measuring line (23).

20. Device according to claim 14, wherein a plurality of immersion tubes (9, 10, 44) and a number of pressure sensors (16, 47), which is one less than the number of immersion tubes, is provided for measuring the pressure difference between the immersion tubes (9, 10, 44) of an immersion tube pair, wherein the immersion tube pairs assigned to the pressure sensors (16, 47) delimit with their corresponding gas depths (21, 22, 48) layers of the electrolyte (4) at different depths, so that the measured data supplied by the pressure sensors (16, 47) can be assigned to the layers.

21. Device according to claim 4, wherein the corresponding electrode connecting line (12, 20, 46) is made of copper or graphite, and is connected to the corresponding electrode (11, 19, 45) by means of a soldering or welding seam (50).

22. Device according to claim 4, wherein the corresponding electrode (11, 19, 45) is configured as a layer of an end area of the corresponding electrode connecting line (12, 20, 46), whose coated section is enclosed by an acid-resistant insulation (49).

23. Device according to claim 4, wherein the corresponding electrode (11, 19, 45) is configured as a coating of an end area of the inner wall of the corresponding immersion tube (9, 10, 44), to which is electrically conductively connected a coating acting as an electrode connecting line (12, 20, 46).

24. Device according to claim 1, comprising a temperature sensor (8) submerged in the electrolyte (4), wherein the temperature sensor (8) and the or each pressure sensor (16, 47) is connected for digitalizing measurement signals to a data processing (25), which is connected via a data bus (27) to a microcontroller (26) for calculating the charge state from the measured acid density of the accumulator (1).

25. Device according to claim 24, which has an elastic outer hose (58), which encompasses as a support two immersion tubes (9, 10), a sleeve tube (43), the temperature sensor (8), and a temperature measuring line (23).

26. Device according to claim 1, wherein two immersion tubes (9, 10) have different diameters, wherein the first immersion tube (9) extends at least partially into the second immersion tube (10).

* * * * *